United States Patent
Lee et al.

(10) Patent No.: US 7,311,903 B2
(45) Date of Patent: Dec. 25, 2007

(54) GLYCOSYLATED HUMAN INTERFERON ALPHA ISOFORM

(75) Inventors: Eun Jung Lee, Gyeonggi-do (KR); Hyung Ki Park, Seoul (KR); Hyun Seok Kim, Seoul (KR); Ji Sook Park, Seoul (KR); Yeon Hyang Kim, Seoul (KR); Hyune Soo Lee, Seoul (KR); Hyung Kon Koh, Seoul (KR); Myung Suk Oh, Gyeonggi-do (KR)

(73) Assignee: CJ Corporation, Seoul (KR)

( * ) Notice: Subject to any disclaimer, the term of this patent is extended or adjusted under 35 U.S.C. 154(b) by 513 days.

(21) Appl. No.: 10/653,350

(22) Filed: Sep. 2, 2003

(65) Prior Publication Data

US 2005/0019871 A1    Jan. 27, 2005

(30) Foreign Application Priority Data

Aug. 31, 2002    (KR) .................. 10-2002-0052365

(51) Int. Cl.
*A61K 38/21*    (2006.01)
*C07K 17/00*    (2006.01)

(52) U.S. Cl. ..................... 424/85.7; 530/351
(58) Field of Classification Search ..................... None
See application file for complete search history.

(56) References Cited

U.S. PATENT DOCUMENTS

| | | | | |
|---|---|---|---|---|
| 4,931,373 A | | 6/1990 | Kawasaki et al. ......... | 435/69.2 |
| 6,020,465 A | * | 2/2000 | Sekellick et al. ........... | 530/351 |
| 6,359,118 B2 | * | 3/2002 | Margolin et al. ........... | 530/395 |
| 6,399,103 B1 | | 6/2002 | Yamagata et al. .......... | 424/489 |
| 6,482,613 B1 | * | 11/2002 | Goeddel et al. ......... | 435/69.51 |

FOREIGN PATENT DOCUMENTS

WO         9848840         11/1998

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Apweiler et al. On the frequency of protein glycosylation, as deduced from the analysis of the SWISS-PROT database (1999), BBA, vol. 1473, pp. 4-8.*
Nyman et al. Identification of nine interferon-alpha subtypes produced by sendai virus induced human peripheral blood leucocytes (1998), biochem. J., vol. 329, pp. 295-302.*
Radhakrishnan et al., (1996)"Zinc mediated dimer of human interferon-$\beta_{2b}$ revealed by X-ray crystallography", Structure vol. 4, 1453-1463.
Adolf et al., (1991) "Natural human interferon-$\alpha 2$ is O-glycosylated", Biochem. J., 276 (Pt 2), 511-518.
Sambrook, J. Fritsch, E.F., Maniatis, T., (1989) Molecular Cloning A Laboratory Manual, 2nd Edition, Cold Spring Harbor Laboratory Press, Cold Spring Harbor, New York.
DeMaeyer and DeMaeyer-Guignard, (1988) Interferons and other regulatory cytokines, Wiley, New York.
Tovey et al. (1987) "Interferon messenger RNA is produced constitutively in the organs of normal individuals", Proc Natl Acad Sci USA, vol. 84, 5038-5042.
Pestka et al. (1982) "Interferons and their actions", Annu. Rev. Biochem., 56, 727-777.
Davis et al. (1986) Basic Methods in Molecular Biology, Elsevier Science Publishing Co.
Lengyel P. (1982) "Biochemistry of interferons and their actions", Annu. Rev. Biochem., 51, 251-282.
Branca and Baglioni (1981) "Evidence that types I and II interferons have different receptors", Nature 294, 768-770.
Isaacs and Lindenmann (1957) "Virus interference. I. The interferon", National Institute for Medical Research, London, 258-267.

* cited by examiner

*Primary Examiner*—Christine J. Saoud
*Assistant Examiner*—Jegatheesan Seharaseyon
(74) *Attorney, Agent, or Firm*—Arent Fox LLP

(57) ABSTRACT

The present invention relates to an amino acid-modified human interferon alpha isoform having at least one of the Asn-Xaa-Ser/Thr (N-X-S/T) sequence formed at a specific site so that glycosylation takes place at this site and a gene encoding the same, an expression vector comprising the gene, and a method for producing glycosylated human interferon alpha isoform by transforming or transfecting an eukaryotic cell with the expression vector, culturing the transfected or transformed cell and isolating the glycosylated human interferon alpha isoform from the culture, the glycosylated human interferon alpha isoform produced therefrom and a pharmaceutical composition comprising the same.

5 Claims, 9 Drawing Sheets

Fig. 1

1. Marker
2. O-Glycosylated IFN-alpha
3. L26N
4. L26N/H34NF36S
5. H34NF36S
6. K134N
7. L26N/K134N

GLYCOSYLATED HUMAN INTERFERON ALPHA ISOFORM

This application claims priority to Korean Patent Application No. 10-2002-0052365 filed on Aug. 31, 2002 the contents of which are incorporated herein in their entirety by reference.

INTRODUCTION

The present invention relates to a glycosylated human interferon alpha isoform. More particularly, the present invention relates to a human interferon alpha isoform having at least one amino acid modified with another amino acid to increase Asn-Xaa-Ser/Thr (N-X-S/T) sequence at a specific region, thereby increasing in vivo stability, and glycosylated human interferon alpha isoform thereof.

BACKGROUND

Interferon was discovered by Isaacs and Lindenmann (Proc. R Soc. Lond[Biol.], 1957, 147, 258-267) in 1957 and has been known to have strong anti-viral effects.

Interferon is classified into type I interferon, including interferon-alpha/-beta, and type II interferon, including interferon gamma. Interferon-alpha is derived from either B lymphocytes or macrophages, interferon-beta is derived from fibroblasts and interferon-gamma is derived from T lymphocytes.

In human, at least 20 kinds of interferon-alpha genes and pseudo-genes have been identified. Proteins of these interferon-alphas are shown to have two disulfide bonds (Cys1-Cys98; Cys29-Cys138) in common. Human interferon-alpha does not contain an N-type glycosylation site but wild type mature protein contains an O-type glycosylation site at Thr106 (Adolf et al., Biochem. J., 276 (Pt 2), 511-518, 1991).

Interferon-alpha can be produced in cells of many tissues, however the yield is very low. Generally, it is produced largely in leucocytes such as monocyte/macrophage and B lymphocyte. Here, the proportion of subtypes of interferons produced depends on the cell type and production conditions. It has been known that the production of interferons is induced by virus infection. Further, bacteria, mycoplasma, protozoa and the like may induce the production of interferon and particularly, lipopolysaccharide (LPS) of gram negative bacteria is a strong interferon inducing agent.

Interferon-alpha mRNA is continuously produced even in tissues of a normal human (Tovey et al., Proc Natl Acad Sci USA, 1987, vol. 84, 5038-5042). It is believed that this interferon is an autocrine interferon playing a important role in cell growth and differentiation.

The working mechanism in vivo of interferon is not known yet. According to the report by Branca and Baglioni (Nature, 294, 768-770, 1981), it was shown that interferon-alpha and -beta bind the same receptor in human lymphoblastoid cell.

When virus infection takes place in vivo, interferon is produced and the produced interferon induced proteins, which perform interferon's functions. Representative examples of such induced proteins include 2'-5'-oligoadenylate synthetase and protein kinase phosphorylation of eIF2 (elongation factor2) which is a factor involved in initiation of peptide chain synthesis. The two enzymes are activated by double-stranded RNA (Lengyel P., Annu. Rev. Biochem., 51, 251-282, 1982; PestKa et. al., Annu. Rev. Biochem., 56, 727-777, 1982; De Maeyer and De Maeyer-Guignard J., interferons and other regulatory cytokines, Wiley, New York).

Interferon is clinically applied to treat chronic active hepatitis B, acute viral encephalitides, nasopharyngeal carcinoma and the like.

Since most of bioactive proteins used as medicaments show low stability in living bodies, patients who need bioactive proteins frequently receive excessive amounts to attain a therapeutic level of the proteins in the body. As a result, some patients suffer pain and inconvenience. Therefore, bioactive proteins having improved in vivo stability are desirable to alleviate the suffering of these patients.

International Patent Application Publication No. WO 98/48840 discloses a preparation of interferon alpha conjugated with polyethyleneglycol as a polymer to increase in vitro stability of bioactive proteins, while U.S. Pat. No. 6,399,103 discloses a preparation of a medicament by microcapsulation of human growth hormone. However, these methods require complicated processes involving primary production of a protein from a microorganism, followed by purification, and subsequent addition reactions. Also, cross-linking may take place at an undesired site leading to problematic heterogeneity of the final product. Another approach is a method using glycosylation.

Cell surface proteins and secretion proteins produced by eukaryotic cells can be modified by glycosylation. It is known that the glycosylation can affect not only physical properties of a protein but also stability and functions of a protein in living bodies.

SUMMARY OF THE INVENTION

The present invention provides methods to readily produce a recombinant human interferon alpha protein with increased in vivo stability. In particular, the invention relates to human interferon alpha isoforms having at least one amino acid modification which increases glycosylation of the protein. The invention provides a recombinant human interferon alpha isoform comprising at least one N-glycosylation motif with the sequence Asn-Xaa-Ser/Thr wherein the asparagine of the motif is N-linked to acetylglucosamine and the motif is in a non-helical region of the protein.

In one aspect, the present invention provides an amino acid-modified human interferon alpha isoform having at least one of the Asn-Xaa-Ser/Thr (N-X-S/T) sequence formed at the following amino acid residue positions so that glycosylation takes place at these sites:

-Cys1-Ser8 (Cys1-Asp-Leu-Pro-Gln-Thr-His-Ser8)
(amino acids 1 to 8 of SEQ ID NO:1);

-Arg22-Thr52 (Arg22-Arg-Ile-Ser-Leu-Phe-Ser-Cys-
Leu-Lys-Asp-Arg-His-Asp-Phe-Gly-Phe-Pro-Gln-Glu-
Glu-Phe-Gly-Asn-Gln-Phe-Gln-Lys-Ala-Glu-Thr52)
(amino acids 22 to 52 of SEQ ID NO:1);

-Ser68 of SEQ ID NO:1;

-Asp77 of SEQ ID NO:1;

-Lys134-Ser136 (Lys134-Tyr-Ser136)
(amino acids 134 to 136 of SEQ ID NO:1);
and

-Gln158-Glu165 (Gln158-Glu-Ser-Leu-Arg-Ser-Lys-
Glu165)
(amino acids 158 to 165 of SEQ ID NO:1).

In another aspect, the present invention provides a gene encoding an amino acid-modified human interferon alpha isoform comprising at least one glycosylation motif, Asn-Xaa-Ser/Thr (N-X-S/T), so that glycosylation takes place at the site.

In a further aspect, the present invention provides an expression vector comprising a gene encoding an amino acid-modified human interferon alpha isoform having at least one Asn-Xaa-Ser/Thr (N-X-S/T) sequence formed at a specific site so that glycosylation takes place at the site.

In yet a further aspect, the present invention provides a transformed or transfected host cell with an expression vector comprising a gene encoding an amino acid-modified human interferon alpha isoform having at least one Asn-Xaa-Ser/Thr (N-X-S/T) sequence formed at a specific site so that glycosylation takes place at the site.

In yet a further aspect, the present invention provides a method for preparing glycosylated human interferon alpha comprising culturing a transformed or transfected host cell with an expression vector comprising a gene encoding an amino acid-modified human interferon alpha isoform having at least one of the Asn-Xaa-Ser/Thr (N-X-S/T) sequence formed at a specific site so that glycosylation takes place at the site in a suitable medium under suitable conditions and isolating the expressed glycosylated human interferon alpha isoform.

In yet a further aspect, the present invention provides glycosylated human interferon alpha isoform obtainable by additional glycosylation of an amino acid-modified human interferon alpha isoform having at least one of the Asn-Xaa-Ser/Thr (N-X-S/T) sequence formed at a specific site so that glycosylation takes place at the site.

In yet a further aspect, the present invention provides a pharmaceutical composition comprising a glycosylated human interferon alpha isoform obtainable by additional glycosylation of an amino acid-modified human interferon alpha isoform having at least one of the Asn-Xaa-Ser/Thr (N-X-S/T) sequence formed at a specific site so that glycosylation takes place at the site and a pharmaceutically acceptable carrier.

In yet another aspect, the present invention provides a synthetic oligodeoxynucleotide used as a primer for production of a glycosylation site in human interferon alpha protein.

The glycosylated human interferon alpha isoform according to the present invention has increased in vivo stability, thereby allowing the dose and/or frequency of administration to be reduced in some clinical applications.

BRIEF DESCRIPTION OF THE DRAWINGS

Further objects and advantages of the invention can be more fully understood from the following detailed description taken in conjunction with the accompanying drawings in which:

FIG. 1 shows the nucleotide sequence (SEQ ID NO:3) and encoded amino acid sequence (SEQ ID NO:1) of a human interferon alpha gene and protein. The arrows over the sequence represent regions of a helical configuration in the three-dimensional structure of human interferon alpha protein. The arrow direction represents the direction of the helix according to the order of the amino acid sequence. Nucleotide numbering appears at the left side of the image while amino acid numbering appears above each sequence paragraph. Arg23 of mature interferon alpha, has a DNA sequence different from that of the known to the art but encodes the same amino acid. Mature interferon alpha protein has an O-glycosylation site at Thr106.

DETAILED DESCRIPTION OF THE INVENTION

Figure 2:
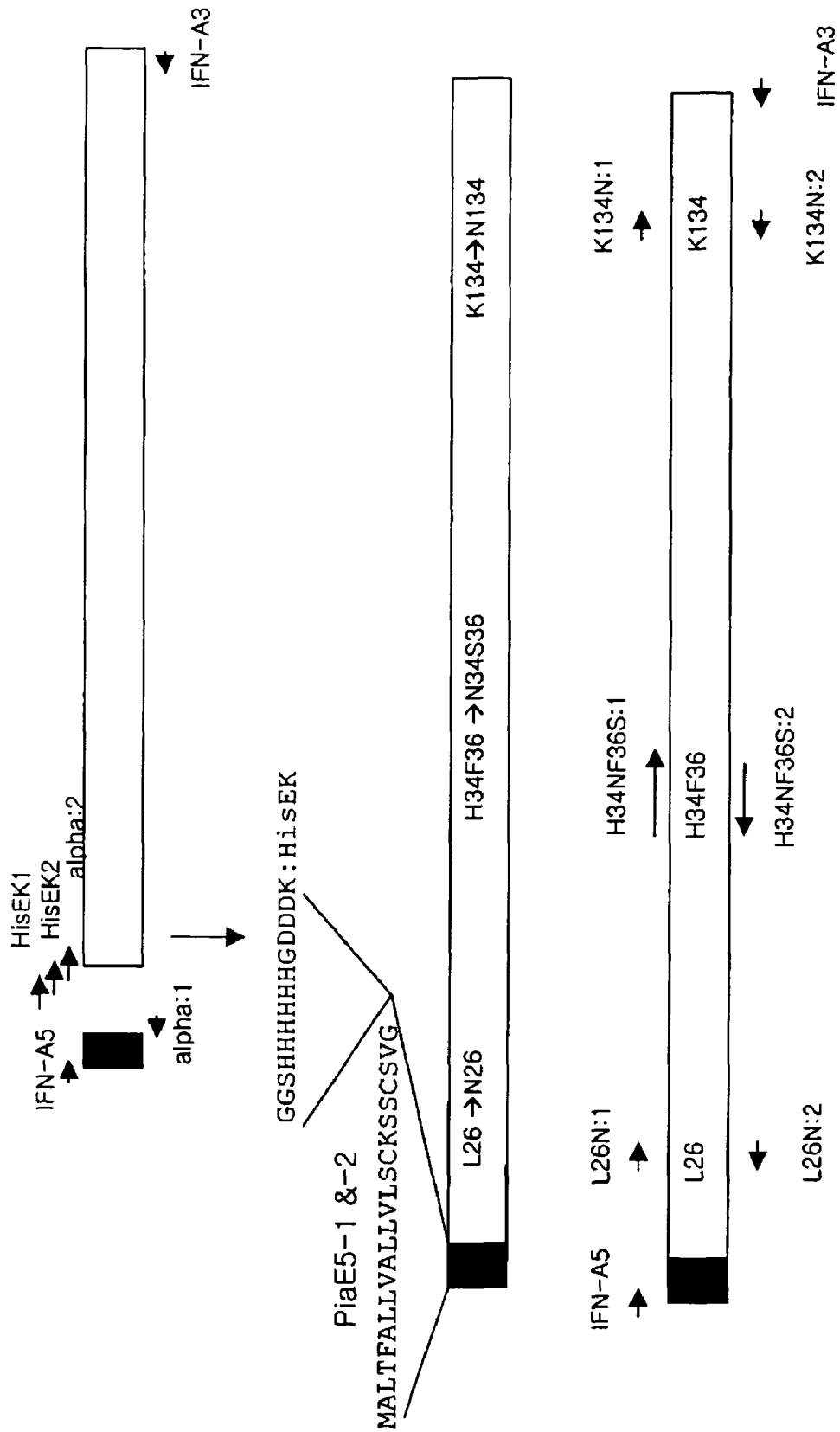
FIG. 2 shows a site in the protein structure of human interferon alpha where amino acid modification of glycosylation according to the present invention takes place, in which the site contains the pre-sequence (amino acids 1-23 of SEQ ID NO:1), 6 histidines as amino acids capable of bonding to a metal ion for readiness of purification and an enterokinase digested site (4 aspartic acids and subsequent lysine sequence) (collectively a histidine tag; SEQ ID NO:2)

The term "isoform of human interferon alpha" used herein refers to an analogue or mutant having one or more of amino acid sequence residues of wild-type human interferon alpha modified with another amino acid while maintaining its inherent activities. Interferon alpha activity may be measured by any assay known in the art. Similarly, interferon alpha stability may be measured by any assay known in the art. In some embodiments of the invention, some reduction in interferon alpha activity relative to wild type may be tolerated provided that there is an off-setting gain in stability.

The standard amino acid abbreviations known in the biochemistry field and used throughout this specification include:

Ala (A): alanine; Asx (B): asparagine or aspartic acid; Cys (C): cystein;

Asp (D): aspartic acid; Glu (E): glutamic acid; Phe (F): phenylalanine;

Gly (G): glycine; His (H): histidine; Ile (I): isoleucine; Lys (K): lysine;

Leu (L): leucine; Met (M): methionine; Asn (N): asparagine; Pro (P): proline;

Gln (Q): glutamine; Arg (R): arginine; Ser (S): serine; Thr (T): threonine;

Val (V): valine; Trp (W): tryptopan; Tyr (Y): tyrosine; Glx (Z): glutamine or glutamic acid.

The notation "(amino acid single letter) (amino acid position) (amino acid single letter)" used herein means that the former amino acid at the corresponding amino acid position of human interferon alpha is substituted with the latter amino acid. For example, L26N indicates that the leucine at amino acid 26 of wild-type human interferon alpha has been replaced with asparagine.

In the present specification, a primer for production of glycosylation site is expressed as "(amino acid single letter) (amino acid position) (amino acid single letter) 1 or 2", in which 1 is a primer complementary to a single strand template proceeding 5'→3' direction in a double strand template and 2 is a primer complementary to a single strand template proceeding 3'→5' direction in a double strand template.

Eukaryotic host cells may secrete proteins comprising at least one oligosaccharide. It is known that such modification, called glycosylation, may enormously affect the physical properties of such modified proteins and be critical in stability, secretion and location of the proteins in a cell. Proper glycosylation may be necessary for biological activity. For example, expression of eukaryotic genes encoding secretory proteins in bacteria, which lack the ability to glycosylate proteins, often yields a protein with deteriorated activity due to the lack of glycosylation.

The glycosylation takes place at a certain position depending on a polypeptide backbone, typically including two types. One is O-type glycosylation which involves binding of oligosaccharide to —OH group of serine or threonine residue and the other is N-type glycosylation which involves binding of oligosaccharide to —NH group of asparagine residue. Particularly, the N-type glycosylation takes place in a specific amino acid sequence and the sequence is known as Asn-Xaa-Ser/Thr (N-X-S/T), in which X may be any amino acid except proline. The N-linked oligosaccharide and the O-linked oligosaccharide have different structures and the residues found in each type are also different from each other. For example, in the O-linked saccharide residue, N-acetylgalactosamine is always bonded to serine or threonine while in the N-linked saccharide residue, N-acetylglucosamine is always bonded to asparagines. The O-linked oligosaccharide generally comprises 4 or less saccharide residues while the N-linked oligosaccharide always contains N-acetylglucosamine and mannose and comprises at least 5 saccharide residues.

The present invention relates to a recombinant human interferon alpha isoform with increased in vivo stability comprising at least one glycosylation motif Asn-Xaa-Ser/Thr (N-X-S/T) sequence at a specific site so that glycosylation takes place at the site.

The present inventors have discovered that glycosylation may be induced by amino acid modification at any region in the amino acid sequence of human interferon alpha protein except for the helical region.

In one embodiment, the present invention is directed to an amino acid-modified human interferon alpha isoform having at least one of the Asn-Xaa-Ser/Thr (N-X-S/T) sequence formed at the following amino acid residue positions so that glycosylation takes place at these sites:

```
-Cys1-Ser8 (Cys1-Asp-Leu-Pro-Gln-Thr-His-Ser8)
(amino acids 1 to 8 of SEQ ID NO:1);

-Arg22-Thr52 (Arg22-Arg-Ile-Ser-Leu-Phe-Ser-Cys-
Leu-Lys-Asp-Arg-His-Asp-Phe-Gly-Phe-Pro-Gln-Glu-
Glu-Phe-Gly-Asn-Gln-Phe-Gln-Lys-Ala-Glu-Thr52)
```

-continued

```
(amino acids 22 to 52 of SEQ ID NO:1);

-Ser68 of SEQ ID NO:1;

-Asp77 of SEQ ID NO:1;

-Lys134-Ser136 (Lys134-Tyr-Ser136)
(amino acids 134 to 136 of SEQ ID NO:1);
and

-Gln158-Glu165 (Gln158-Glu-Ser-Leu-Arg-Ser-Lys-
Glu165)
(amino acids 158 to 165 of SEQ ID NO:1).
```

In a preferred embodiment, the present invention is directed to an amino acid-modified human interferon alpha isoform having at least one of the Asn-Xaa-Ser/Thr (N-X-S/T) sequence formed at the following amino acid residue positions so that glycosylation takes place at these sites:

```
-Arg22-Thr52 (Arg22-Arg-Ile-Ser-Leu-Phe-Ser-Cys-
Leu-Lys-Asp-Arg-His-Asp-Phe-Gly-Phe-Pro-Gln-Glu-
Glu-Phe-Gly-Asn-Gln-Phe-Gln-Lys-Ala-Glu-Thr52)
(amino acids 22 to 52 of SEQ ID NO:1);
and -Lys134-Ser136 (Lys134-Tyr-Ser136).
```

In a more preferred embodiment, the present invention is directed to an amino acid-modified human interferon alpha isoform having one or more of the following modifications Leu26 modified with asparagine, His34 and Phe36 modified with asparagine and serine, respectively, or Lys134 modified with asparagine. Additionally, the present invention is directed to an amino acid modified human interferon alpha isoform having all of these modifications.

The present invention encompasses modifying at least one nucleotide of a DNA so that the encoded human interferon alpha has an additional glycosylation site, introducing the DNA to an eukaryotic cell carrying out the glycosylation, followed by expression so that the additional glycosylation naturally occurs. The additionally glycosylated human interferon alpha according to the present invention is achieved by modifying the DNA sequence so that the occurrence of the sequence motif Asn-Xaa-Ser/Thr (N-X-S/T) is increased.

In one embodiment, the present invention is directed to a gene encoding an amino acid-modified human interferon alpha isoform having at least one glycosylation motif Asn-Xaa-Ser/Thr (N-X-S/T) sequence formed at the following amino acid residue positions so that glycosylation takes place at these sites:

```
-Cys1-Ser8 (Cys1-Asp-Leu-Pro-Gln-Thr-His-Ser8)
(amino acids 1 to 8 of SEQ ID NO:1);

-Arg22-Thr52 (Arg22-Arg-Ile-Ser-Leu-Phe-Ser-Cys-
Leu-Lys-Asp-Arg-His-Asp-Phe-Gly-Phe-Pro-Gln-Glu-
Glu-Phe-Gly-Asn-Gln-Phe-Gln-Lys-Ala-Glu-Thr52)
(amino acids 22 to 52 of SEQ ID NO:1);

-Ser68 of SEQ ID NO:1;

-Asp77 of SEQ ID NO:1;

-Lys134-Ser136 (Lys134-Tyr-Ser136)
(amino acids 134 to 136 of SEQ ID NO:1);
```

-continued and -Gln158-Glu165 (Gln158-Glu-Ser-Leu-Arg-Ser-Lys-
Glu165)
(amino acids 158 to 165 of SEQ ID NO:1).

In a preferred embodiment, the present invention is directed to a gene encoding an amino acid-modified human interferon alpha isoform having at least one amino acid modified with another amino acid so that the Asn-Xaa-Ser/Thr (N-X-S/T) sequence is increased at the following amino acid residue positions:

-Arg22-Thr52 (Arg22-Arg-Ile-Ser-Leu-Phe-Ser-Cys-
Leu-Lys-Asp-Arg-His-Asp-Phe-Gly-Phe-Pro-Gln-Glu-
Glu-Phe-Gly-Asn-Gln-Phe-Gln-Lys-Ala-Glu-Thr52)
(amino acids 22 to 52 of SEQ ID NO:1);
and -Lys134-Ser136 (Lys134-Tyr-Ser136).

In a more preferred embodiment, the present invention is directed to a gene encoding an amino acid-modified human interferon alpha isoform having Leu26 modified with asparagine, His34 and Phe36 modified with asparagine and serine, respectively, or Lys134 modified with asparagine, or having all of these modifications.

In one embodiment of the present invention, the gene encoding human interferon alpha is obtained from human interferon alpha-producing strain for animal cell expression. Methods known to the art may be used for gene cloning and separation.

The human interferon alpha gene obtained from the above may be modified in at least one selected codon. In the present specification, modification may be defined as substitution of one or more codon(s) on a gene encoding human interferon alpha to make a change in the amino acid sequence of human interferon alpha. More particularly, it refers to substitution of at least one amino acid with another amino acid so that the Asn-Xaa-Ser/Thr (N-X-S/T) sequence for additional N-type glycosylation is formed on the amino acid sequence of human interferon alpha. For example, in Example 3 of the present invention, when Leu26 is substituted with asparagine, since amino acid residue 28 is serine, the Asn-Xaa-Ser/Thr (N-X-S/T) sequence is formed, whereby an additional N-type glycosylation may take place. Also, when His34 and Phe36 are substituted with asparagine and serine, respectively, the Asn-Xaa-Ser/Thr (N-X-S/T) sequence is formed, whereby an additional N-type glycosylation may take place. Further, when Lys134 is substituted with asparagine, since amino acid residue 136 is serine, the Asn-Xaa-Ser/Thr (N-X-S/T) sequence is formed, whereby an additional N-type glycosylation may take place.

In one embodiment, a synthetic oligonucleotide comprising a codon encoding a desired amino acid modification in human interferon alpha is constructed. Typically, an oligonucleotide having a length of about 25 nucleotides is used, although shorter oligonucleotides may be used. In some embodiments the optimal oligonucleotide has 12 to 15 nucleotides complementary to a template flanking each side of the nucleotides encoding the modification. Such oligonucleotides may be sufficiently hybridized to the template DNA. Some synthetic oligonucleotides used for production of an additional glycosylation site in the present invention are shown in Table 2. These oligonucleotides can be synthesized by techniques known in the art.

In one embodiment of the present invention, there is provided a nucleic acid molecule encoding human interferon alpha isoform with one amino acid modified. PCR is conducted using human interferon alpha DNA as a template and a synthetic oligonucleotide encoding a modification as a primer. In the heating step of PCR, the double stranded template is separated and a complementary primer is hybridized to each of the template single strands. DNA polymerase adds nucleotides complementary to the template from —OH group of the primer encoding the modification in 5'→3' direction. Consequently, the second strand contains the primer encoding the modification and thus encodes the desired modification on a gene. The second strand serves as a template DNA in the repeated replication steps of PCR and the gene encoding the modification will be continuously amplified. For example, in Example 3 of the present invention, in order to modify Leu26 with asparagine, PCR is conducted using wild-type interferon alpha DNA as a template and primer pairs of IFN-A5' and L26N2, and L26N1 and IFN-A3'. As a result, two DNA segments, in which amino acid residue 26 is changed to a codon corresponding to asparagine instead of leucine, are obtained. Then, secondary PCR is conducted using the two DNA segments thus obtained and IFN-A5' and IFN-A3' as a primer pair to obtain a modified gene of IFN-alpha-L26N, in which amino acid residue 26 is modified with asparagine instead of leucine so glycosylation may occur.

In another embodiment of the present invention, there is provided a human interferon alpha isoform comprising two or more amino acid modifications. These modifications may be the same or different. A mutant having two or more amino acids modified is constructed by various methods. When the two or more amino acids to be modified are adjacent to each other on a polypeptide, they can be simultaneously modified using an oligonucleotide having all the amino acid modifications encoded. Therefore, the construction of such a mutant is the same as the method for construction of a human interferon alpha gene with one nucleotide modified except that an oligonucleotide having two or more amino acid modifications is used as a primer. However, when the two or more amino acids are far from each other on a polypeptide (spaced by 10 or more amino acids), it is impossible to construct a single oligonucleotide primer having all the desired modifications encoded.

In such instances, other methods should be utilized for construction of the mutant. The first method is to construct individual oligonucleotides containing each amino acid modification. If the oligonucleotides are simultaneously annealed to a single strand template DNA, the second strand DNA synthesized from the template will encode all the desired amino acid modifications. Another method in the present invention includes two or more mutagenesis steps to produce such an isoform. In the first mutagenesis, wild-type DNA is used as a template and an oligonucleotide containing the first desired amino acid modification is annealed to the template to form a heterogeneous DNA (heteroduplex). In the second mutagenesis, the modified DNA, prepared in the first mutagenesis, is used as a template. Thus, this template already contains at least one modification. To this template, an oligonucleotide containing an additional amino acid modification is annealed and the resulting DNA will have all the modifications of the first and second mutagenesis encoded. The resulting DNA can be used as a template in the third mutagenesis.

In summary, the foregoing method for modifying two or more nucleotides is to repeat a method for modifying one nucleotide several times. For example, in Example 3 of the present invention, to modify Leu26 of wild-type interferon alpha protein with asparagine and Lys134 with asparagine at the same time, first amino acid residue 134 is modified and then amino acid residue 26 is modified using the previously modified DNA as a template. As a result, a human interferon alpha gene having the two residues modified is obtained.

In some embodiments of the invention, a recombinant interferon is provided which has at least one added N-glycosylation site according to the invention and one further modification. The additional modification(s) may be any amino acid modification or other modification known in the art or herein described. For example, the additional modification may facilitate purification of the recombinant protein such as the addition of a histidine tag.

The DNA sequences encoding the human interferon alpha isoforms according to the present invention can be synthesized by any standard method known to the art, for example using an automatic DNA synthesizer (ex. Biosearch, Applied Biosystem™).

The glycosylated isoform according to the present invention is typically produced by inserting the DNA sequence encoding a human interferon alpha isoform into a vector having one or more expression control sequences operatively linked to the DNA sequence to control its expression, transforming or transfecting a host with the resulting recombinant expression vector, culturing the transformed or transfected cell in a proper medium and condition to express the human interferon alpha isoform DNA sequence, followed by isolation of the glycosylated human interferon alpha isoform.

In connection with this, the present invention provides a host cell transformed or transfected with the recombinant expression vector containing the DNA sequence encoding the human interferon alpha isoform.

Of course, it should be understood that all the vectors and expression control sequences do not function equally to express the DNA sequences according to the present invention. Similarly, all the host cells do not function equally for the same expression system. However, those skilled in the art may properly select a vector, expression control sequence and host cell without departing from the scope of the present invention and without undue experimentation. For example, in selection of a vector, a host cell must be considered. This is because the vector should be replicated therein. Also, the replication number and ability to control the replication number of a vector and expression of other proteins encoded by the vector, for example antibiotic marker should be considered. In selection of an expression control sequence, various factors should be considered. For example, relative strength of the sequence, controllability and compatibility with the DNA sequence of the present invention, particularly with respect to a possible two-dimensional structure should be considered. Also, in selection of a host, compatibility with a selected vector, toxicity, secretion properties and ability to correctly fold a polypeptide of the product encoded by the nucleotide sequence, fermentation or cultivation requirements and conditions and readiness of purification of the product encoded by the nucleotide sequence.

The term "vector" used herein refers to a DNA molecule as a carrier capable of stably carrying a foreign gene into a host cell. In order to be a useful vector, a vector can be replicated, has a means to be introduced into a host cell and to detect its own presence.

The term "recombinant expression vector" refers to a cyclic DNA molecule, in which a gene of interest is operably linked to at least one expression sequence so that the gene can be expressed in a host cell. The recombinant expression vector can be produced as several copies and heterogeneous DNA inserted therein. As well-known to the art, in order to increase expression level of a transfected gene in a host cell, the gene should be operably linked to an open frame expression control sequence which can work in a selected expression host. Preferably, the gene is contained in an expression vector comprising a selection marker and replication origin. When an expression host is a eukaryotic cell, the expression vector should further comprise an expression marker useful in the eukaryotic expression host cell.

Various expression vectors can be used to express the DNA sequence encoding the human interferon alpha isoform. Preferably, an expression vector suitable for an eukaryotic host cell is used since glycosylation takes place on the human interferon alpha isoform.

Examples of expression vectors useful for eukaryotic host cells include expression control sequences derived from SV40, bovine papilloma virus, adenovirus and cytomegalovirus. Specific examples of the vectors include pCDNA3.1 (+) Hyg (Invitrogen, Carlsbad, Calif., USA) and pCI-neo (Stratagene, La Jolla, Calif., USA). Expression vectors useful for yeast cells include 2μ plasmid and derivatives thereof, POT1 vector (U.S. Pat. No. 4,931,373) and pPICZ A, B, or C (Invitrogen). Expression vectors useful for insect cells include pVL 941, pBluebac 4.5 and pMelbac (Invitrogen).

"Expression control sequence" refers to nucleic acid sequences necessary or beneficial to polypeptide expression. Respective expression control sequences can be a native or foreign on a nucleic acid encoding a polypeptide. Examples of the control sequence include, but are not limited thereto, leader sequence, polyadenylated sequence, propeptide sequence, promoter, enhancer or upstream activation sequence, signal peptide sequence and transcription termination factor. An expression control sequence contains a promoter.

In order to express the DNA sequence of the present invention, various expression control sequences can be used in the vectors. Examples of expression control sequences suitable to promote expression in mammal cells include early and late promoters of SV40 and adenovirus, MT-1 (metallothioneine gene) promoter, human cytomegalovirus early gene (CMV), Raus sarcoma virus (RSV) promoter and human Ubiquitine C (UbC) promoter. In order to further improve expression in mammalian cells, synthetic intron sequences can be inserted into a non-transcription region of a nucleotide sequence encoding a polypeptide.

Examples of expression control sequences suitable to promote expression in insect cells include polyhedrin promoter, P10 promoter, baculovirus 39K delayed-early gene promoter and SV40 polyadenylation sequence. Examples of expression control sequences usable in yeast cells include a promoter of α-mating system, yeast triose phosphate isomerization enzyme (TPI) promoter and ADH2-4c promoter. Examples of expression control sequences suitable to instruct expression in fungus cells include ADH3 promoter and termination factor.

Other vector components used in practicing the present invention include a signal peptide. This sequence is typically located at the 5' of a gene encoding a protein and is thus, added to the amino terminus of the protein. Presence or absence of a signal peptide varies depending on the expression host cell used in production of a polypeptide to be expressed (according to whether the polypeptide to be expressed is intracell or extracell polypeptide) and preference of recovering secreted products. The signal peptide exists when a polypeptide is secreted from a expressed cell.

If the signal peptide exists, it should be recognized by a cell selected for expression of a polypeptide. The signal peptide can be homologus to a polypeptide (typically associated with the polypeptide) or heterologus to a polypeptide (derived from one other than the polypeptide) and can be homologus or heterologus to a host cell.

A nucleic acid is "operably linked" to another nucleic acid when they are arranged in a functional relationship. This means that an appropriate molecule (for example, a transcription activator) binds to a regulatory sequence (s), a gene or a regulatory sequence (s) linked in such a way that the expression of the gene is modulated. For example, when a pre-sequence or secretory leader participates in secretion of a mature protein, they are operably linked to the promoter. When a promoter affects transcription of a coding sequence, the promoter is operably linked to the coding sequence. When a ribosomal binding site is located at a place capable of being read as a coding sequence, the ribosomal binding site is operably linked to the coding sequence. Generally "operably linked" means in contact with a linked DNA and a secretory leader and to be in a reading frame.

However, the enhancer does not need to be in contact. The linkage of these sequences are effected by ligation (linkage) in a convenient restriction enzyme site. If such a site does not exist, a conventionally synthesized oligonucleotide adaptor or linker may be used.

Construction of a suitable vector comprising a gene encoding the human interferon alpha isoform and the foregoing components (i.e. a control sequence) can be performed using a basic recombinant technology. In order to prepare a desired vector, respective DNA segments are firstly digested with restriction enzymes and then ligated to each other considering a particular order and orientation. DNA can be digested using a particular restriction enzyme in a proper buffer.

Typically, about 0.2-1 ug of a plasmid or a DNA segment is used along with about 1 to 2 units of required restriction enzyme in about 20 μl of buffer. A proper buffer, DNA amount, incubation time and temperature are specified by a manufacturer of the restriction enzyme. Typically, it is suitable to incubate for about 1 to 2 hours at 37° C., though some enzymes need a higher temperature. After incubation, enzymes and other impurities can be removed by extraction of the digestion solution with a mixture of phenol and chloroform and DNA can be recovered from the aqueous layer by precipitation with ethanol. Here, ends of the DNA segments are compatible with each other so that the DNA segments can form a functional vector.

The digested DNA segments are classified and selected according to their sizes by electrophoresis. DNA can be electrophoresed through agarose or polyacrylamide matrix. Selection of the matrix can be determined by a size of the DNA segment to be isolated. After electrophoresis, DNA is extracted from the matrix by electroelution. When a low-melting agarose is used, agarose is melted and DNA is extrated therefrom.

The DNA segments to be ligated should be added to the solution in an equal molar amount. The solution contains ATP, ligase buffer, ligases such as about 10 units of T4 ligase per DNA 0.5 ug. In order ligate a DNA segment to a vector, the vector should be linearlized through digestion with a suitable restriction enzyme. The linearlized vector is treated with alkaline phosphatase or calf intestinal alkaline phosphatase. The treatment with phosphorylase inhibits self-ligation of a vector during the ligation step. The recombinant expression vector prepared by the above-described method is then used to transform or transfect a host cell.

In selection of a host cell, a host cell having a high DNA introduction efficiency and showing a high expression efficiency of the introduced DNA is selected. Particularly, in the present invention, eukaryotic host cells capable of glycosylation of the human interferon alpha isoform are used. Suitable examples of yeast host cells include *Saccharomyces* and *Hansenula* strains. Suitable examples of fungus host cells include *Tricoderma*, *Fusarium* and *Aspergillus* strains. Suitable examples of insect host cell include *Lepidoptora* cell lines such as Sf9 or Sf21. Suitable examples of mammal host cells include CHO cell line, COS cell lines such as COS 1, COS 7, BHK cell lines and animal cells such as mouse and human cells, and tissue cultured plant cells.

Polynucleotides can be introduced to a host cell by methods described in basic experiment manuals such as [Davis et al., Basic Methods in Molecular Biology (1986)] and [Sambrook et al., (1989) Molecular Cloning $2^{nd}$ Edition]. Preferred methods for introducing a polynucleotide into a host cell include, for example, calcium phosphate transfection, DEAE-dextran mediated transfection, microinjection, cationic lipid-mediated transfection, electroporation, transduction, scrape loading, ballistic introduction or infection.

In the production method of the present invention, host cells are cultured in a nutrient medium suitable for polypeptide production using a known technology. For example, cells can be cultured in a suitable medium in a fermentor for laboratory or industry under conditions acceptable for expression and/or secretion of a polypeptide by small-scale or large scale fermentation, e.g. shaking flask culture. The cultivation is conducted in a proper nutrient medium comprising carbon, nitrogen supply source and inorganic salts using a known technology. The medium is well known to those skilled in the art and is commercially available or can be produced. When a peptide is directly secreted to a nutrient medium, the polypeptide can be directly isolated from the medium. When a polypeptide is not secreted, it can be isolated from cell lysate.

Polypeptides of the invention can be isolated by a method known to the art. For example, it can be isolated from a nutrient medium by traditional methods including, but not limited thereto, centrifugation, filtration, extraction, spray drying, evaporation or precipitation. Further, a polypeptide can be purified by various methods known to the public including chromatograph (ex. Ion exchange, affinity, hydrophilic, hydrophobic, size-exclusion), electrophoresis, fractional solubility (ex. Ammonium sulfate precipitation), SDS-PAGE or extraction.

The present invention provides a glycosylated human interferon alpha isoform with an additional glycosylation obtainable through the above described procedure. In the present specification, the glycosylated human interferon alpha isoform can be defined as an expression product obtained by introducing a human interferon alpha gene which is modified to increase the Asn-Xaa-Ser/Thr (N-X-S/T) sequence into an eukaryotic host cell, followed by expression so that glycosylation can spontaneously occur. That is, it refers to a heterogenous molecule formed by covalent bonding of sugar residues to the asparagine —NH group of Asn-Xaa-Ser/Thr (N-X-S/T), an additional glycosylation site of the human interferon alpha isoform.

The present invention provides a pharmaceutical composition comprising glycosylated human interferon alpha isoform with an additional glycosylation and a pharmaceutically acceptable carrier. A therapeutic preparation of the glycosylated human interferon alpha isoform for therapeutic administration can be formulated into lyophilized cake and aqueous solution combining any pharmaceutically acceptable carrier, excipient, stabilizer and the glycosylated human interferon alpha isoform having a desired purity. A preparation for parenteral administration can be prepared by combining the glycosylated human interferon alpha isoform with a pharmaceutical carrier into a formulation, which can be administered (solution, suspension or emulsion).

According to the invention pharmaceutically acceptable carriers, excipients and stabilizers should not show toxicity to the recipient at the dose and concentration to be administered. Carriers, recipients, and stabilizers are also compatible with other ingredients. For example, the preparation should not contain an oxidant or other substances, which are known as being harmful to a polypeptide.

Suitable carriers include buffers such as phosphoric acid, citric acid and other organic acids; antioxidants such as ascorbic acid; low-molecular polypeptides; proteins such as serum albumin, gelatin and immunoglobulin; hydrophilic polymers such as polyvinylpyrrolidone; amino acids such as glycine, glutamine, arginine or lysine; monosaccharides such as mannose or dextrin, disaccharides, other carbohydrates; chelating factors such as EDTA; metal ions such as zinc, cobalt or copper; sugar alcohols such as manitol or sorbitol; salt-forming counter ions such as sodium; and/or non-ionic surfactants such as Tween, Pluronic or polyethylene glycol (PEG).

In order to use the glycosylated human interferon alpha isoform for therapeutic administration, it should be sterilized. The sterilization can be readily accomplished by filtration through a sterile filtration membrane.

The therapeutic composition of the glycosylated human interferon alpha isoform is typically stored in a container having a sterile access port, such as, for example, vascular injection bag having a cap through which a subcutaneous injection needle can pass or vial. The human interferon alpha will be stored as an aqueous solution or lyophilized preparation in a single dose or multi-dose container, for example, a sealed vial or an ampoule. In case of the lyophilized preparation, 5 ml of sterilized and filtered 1% (w/v) human interferon alpha aqueous solution is filled in a 10 ml-vial and the mixture is lyophilized. The injection can be prepared by reconstruction of the lyophilized human interferon alpha with bacteriostatic Water-for-Injection.

The glycosylated human interferon alpha isoform can be directly administered to a subject by a proper technology including paranteral administration, or locally or systemically administered. A particular administration route can be determined depending on, for example, a patient's case history including side effects which are recognized or expected by the human interferon alpha. Examples of the parenteral administration include subcutaneous, intramuscular, intravascular, intraarterial, intraperitoneal administration. Most preferably, the administration is carried out by sustained injection (ex. a mini pump such as osmosis pump) or injection through, for example, intravascular or subcutaneous route. The glycosylated human interferon alpha isoform is preferably administered subcutaneously.

The glycosylated human interferon alpha isoform is administered to a patient in a therapeutically effective amount. The term "therapeutically effective amount" can be defined as an amount sufficient to show a desired therapeutic effect in a given condition and administration method. The human interferon alpha composition for treatment should be prepared and administered considering particular conditions to be treated, clinical conditions of individual patients (particularly side effects upon treatment with human interferon alpha along), delivery location of the glycosylated human interferon alpha isoform, administration method, administration schedule, other factors known to those skilled in the art and being consistent with preferred medical practices. The therapeutically effective amount in the treatment with the glycosylated human interferon alpha isoform is determined by the foregoing matters. A daily effective amount of the glycosylated human interferon alpha isoform according to the present invention is in the range of about $2 \times 10^6$ units to $500 \times 10^6$ units.

Now, the present invention will be described in further detail by the following examples. However, the examples are only for illustration of the present invention and the present invention is not limited thereto.

EXAMPLES

Example 1

Preparation of Recombinant Human Interferon Alpha Gene

As human interferon alpha gene, a modified interferon alpha-producing strain possessed by the applicant was used. The interferon alpha gene did not comprise the whole sequence for expression in *E. coli*. Therefore, PCR using chemically synthesized oligodeoxynucleotides was conducted to prepare the whole sequence. The partial human interferon alpha gene was amplified using PiaE5-1 and IFN-A5' synthetic oligodeoxynucleotides. The DNA fragment was amplified by PCR using a synthetic oligodeoxynucleotide of PiaE5-2 and IFN-A3' to introduce a full-length signal sequence at 5'-end of human interferon alpha gene. The utilized synthetic oligodeoxynucleotides are shown in Table 1.

Table 1

Synthetic oligodeoxynucleotides used as primers for construction of full length human interferon alpha sequence

| Primer Name | primer sequence | SEQ ID NO |
|---|---|---|
| PiaE5-1 | 5-'GTGCTCAGCTGCAAGTCAAGCTGCTCTGTGG GCTGTGATCTGCCTCAAACCCAC-3' | 4 |
| PiaE5-2 | 5'-ATGGCCTTGACCTTTGCTTTACTGGTGGCCCT CCTGGTGCTCAGCTGCAAGTCA-3' | 5 |
| IFN-A5' | 5'-TCCCAAGCTTATGGCCTTGACCTTTGCTTT ACTG-3' | 6 |
| IFN-A3' | 5'-TGGGATCCTCATTCCTTACTTCTTAAACTTTC TTG-3' | 7 |
| HisEK:1 | 5'-AAGCTTCCCATGGGGGGTTCTCATCATCATCA TCATCATGGG-3' | 8 |
| HisEK:2 | 5'-CATCATCATCATCATCATGGGGACGATGACG ATAAG-3' | 9 |
| Alpha:1 | 5'-ACCCCCCATGGAGCCCACAGAGCAGCTTGA-3' | 10 |
| Alpha:2 | 5'-GGGGACGATGACGATAAGTGTGATCTGCCTC AAACC-3' | 11 |

Example 2

Selection of Modification Site on Human Interferon Alpha Gene

In order to select a site for additional glycosylation on human interferon alpha, the results of Walter (Structure (1996) vol.4, 1453) were used. In selection of a site, first, the helical region in the amino acid sequence of human interferon alpha protein was excluded (FIG. 2). From the sequence with the helical region excluded, a second site was selected, taking into consideration that Thr106 of wild-type interferon has O-type glycosylation in three-dimension. From the second selected site, a site where N-type glycosylation could be readily converted to a motif was finally selected.

Figure 1:
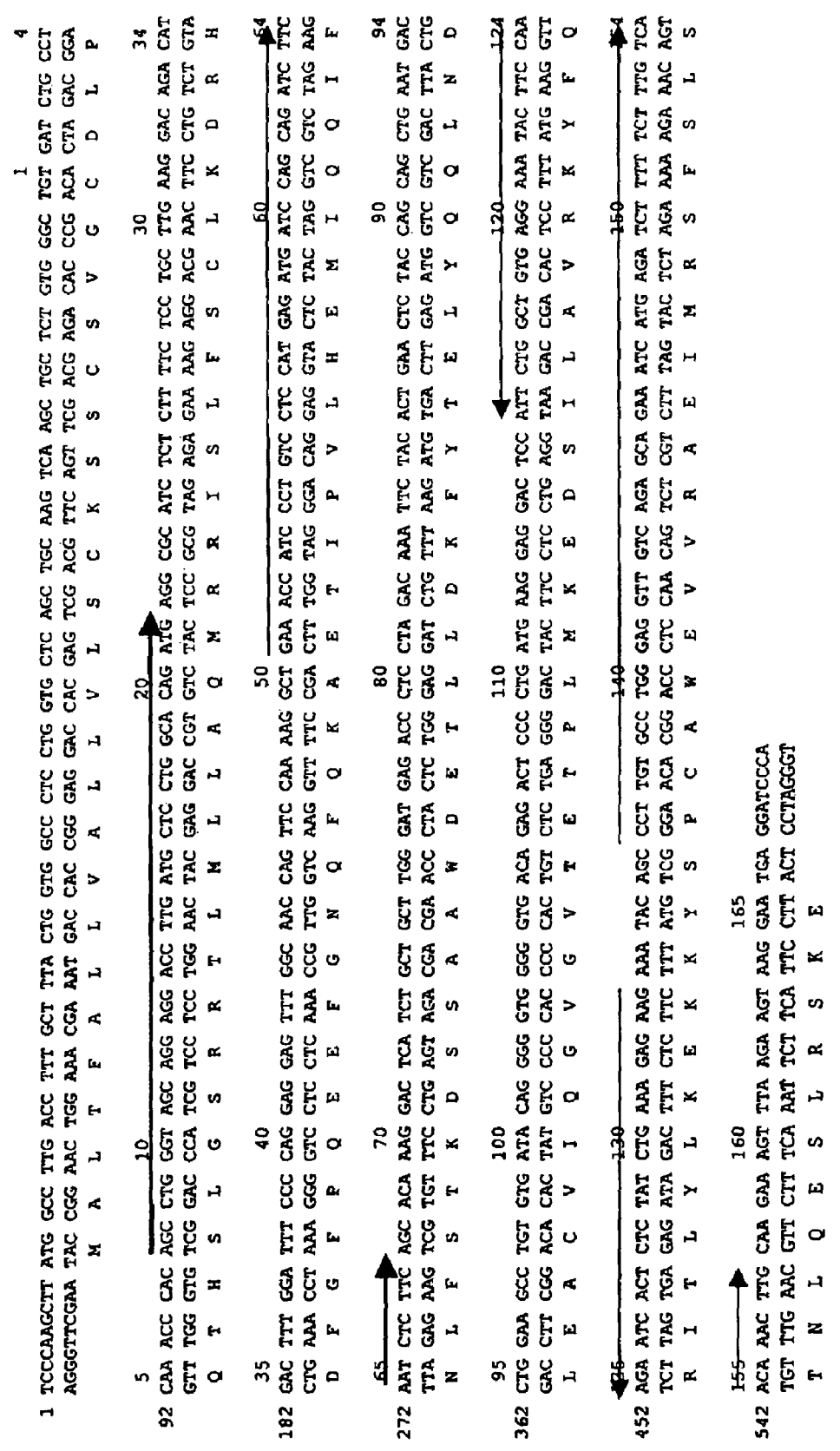

As shown in FIG. 1, the sites selected to attempt modification for addition of an additional glycosylation site were L26, H34 and F36, and K134, in which Leu26 was modified with asparagine, His and Phe36 were modified with asparagine and serine, and the Lys134 was modified with asparagine. The synthetic oligodeoxynucleotides used for this experiment are shown. The direction of the arrow represents of 5'->3' direction of respective oligodeoxy nucleotides.

In order to purify human interferon alpha protein, an additional amino acid sequence (HisEK) was inserted between the pre-sequence and the amino acid sequence of mature human interferon alpha protein. The amino acid sequence was M-G-G-S-H-H-H-H-H-H-G-D-D-D-D-K- (SEQ ID NO:2). By inserting this amino acid sequence, expressed human interferon alpha derivative protein can isolated by metal affinity column chromatography. The isolated protein was treated with enterokinase and subjected to metal affinity column chromatography to obtain only human interferon alpha derivative protein.

The insertion of HisEK sequence was conducted by amplifying DNA at the pre-sequence region by PCR with IFN-A5 and alpha: 1 primer, followed by digestion with restriction enzyme NcoI. Then, the mature human interferon alpha gene region was primarily amplified with alpha:2 and IFN-A3. The resulting DNA segment was secondarily amplified with HisEK:2 and IFN-A3 and then with HisEK:1 and IFN-A3 to obtain a DNA segment. The resulting DNA segment was digested with restriction enzyme NcoI and the resulting two DNA segments were joined using T4 DNA ligase.

The joined human interferon alpha gene was again amplified by PCR using IFN-A5 and IFN-A3 primers. The amplified DNA segment was digested with restriction enzyme HindIII and BamHI and inserted to pcDNA3.1Hygro+ plasmid vector, which had been digested with the same restriction enzymes, using T4 DNA ligase to form an expression vector.

Example 3

Construction of Human Interferon Alpha Isoform

A gene encoding human interferon alpha having at least one amino acid modified to provide an additional glycosylation site can be formed by PCR using synthetic oligodeoxynucleotides as primers. Synthetic oligodeoxynucleotides are shown in Table 2.

TABLE 2

Synthetic oligodeoxynucleotide used for production of additional glycosylation

| primer name | primer sequence | SEQ ID NO |
|---|---|---|
| L26N1 | 5'-GCACAGATGAGGCGCATCTCTAACTTCTCCTG CTTGAAGGACAGA-3' | 12 |

TABLE 2-continued

Synthetic oligodeoxynucleotide used for production of additional glycosylation

| primer name | primer sequence | SEQ ID NO |
|---|---|---|
| L26N2 | 5'-TCTGTCCTTCAAGCAGGAGTTAAGAGAGATGC GCCTCATCTGTGC-3' | 13 |
| H34NF36S:1 | 5'-TTGAAGGACAGAAACGACAGCGGATTTCCCC AG-3' | 14 |
| H34NF36S:2 | 5'-CTTCATCAGGGGAGTCTCGTTCACCCCCACC CC-3' | 15 |
| K134N1 | 5'-ACTCTCTATCTGAAAGAGAAGAACTACAGCCC TTGTGCCTGGGAG-3' | 16 |
| K134N2 | 5'-CTCCCAGGCACAAGGGCTGTAGTTCTTCTCTTT CAGATAGAGAGT-3' | 17 |
| IFN-A5' | 5'-TCCCAAGCTTATGGCCTTGACCTTTGCTTTAC TG-3' | 18 |
| IFN-A3' | 5-'TGGGATCCTCATTCCTTACTTCTTAAACTTTCT TG-3' | 19 |

Figure 3:
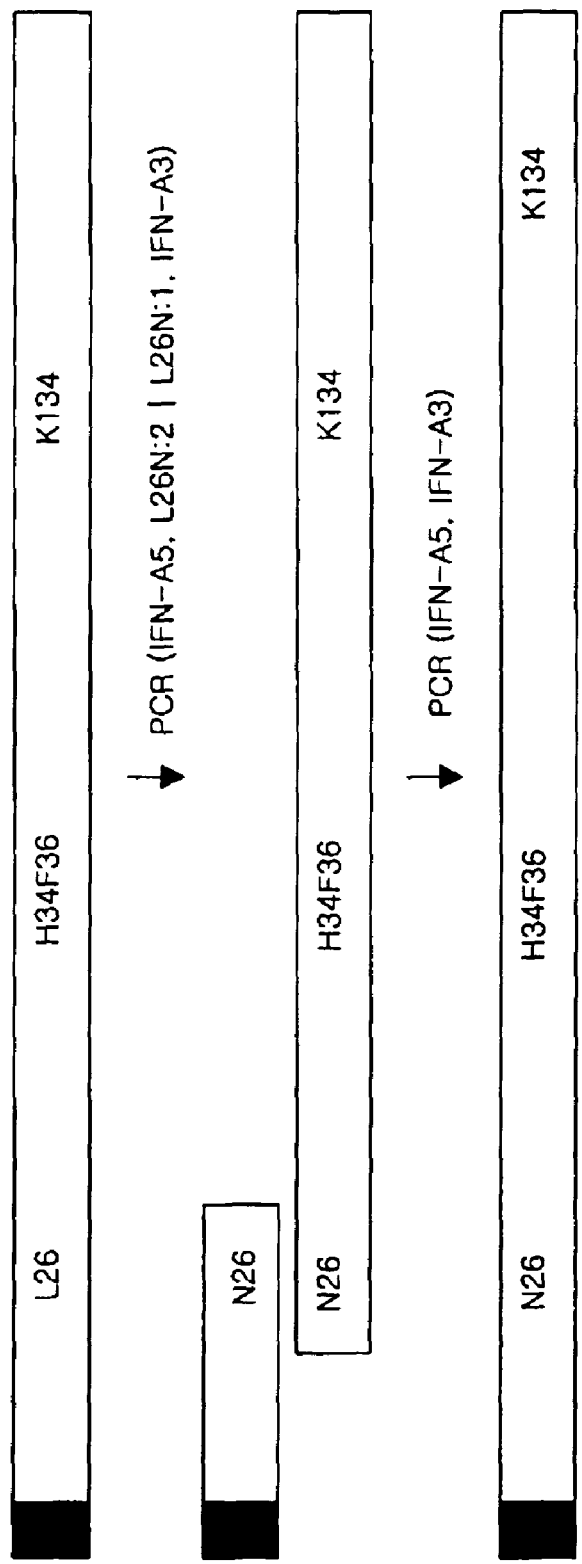
FIG. 3 is a schematic diagram to show the method for modifying Leu26 with asparagine.

(1) Construction of L26N Modified Human Interferon Alpha Isoform (FIG. 3)

The human interferon alpha gene obtained from Example 1 were amplified by PCR with synthetic oligodeoxynucleotide primers, IFN-A5' and L26N2, L26N1 and IFN-A3' to prepare DNA segments. Each of the prepared DNA segments was purified, denatured with 0.2M NaOH/2mM EDTA and subjected to PCR to prepare a gene with an amino acid at a desired site changed (Leu→Asn). As a result, two DNA segments substituted with a codon corresponding to asparagine instead of leucine at the No. 26 amino acid position were obtained. The two DNA segments were subjected to secondary PCR using a primer pair of IFN-A5' and IFN-A3' to obtain a modified gene of IFN-alpha-L26N, in which 26th amino acid is modified with asparagines so that an additional glycosylation can take place.

Figure 4:
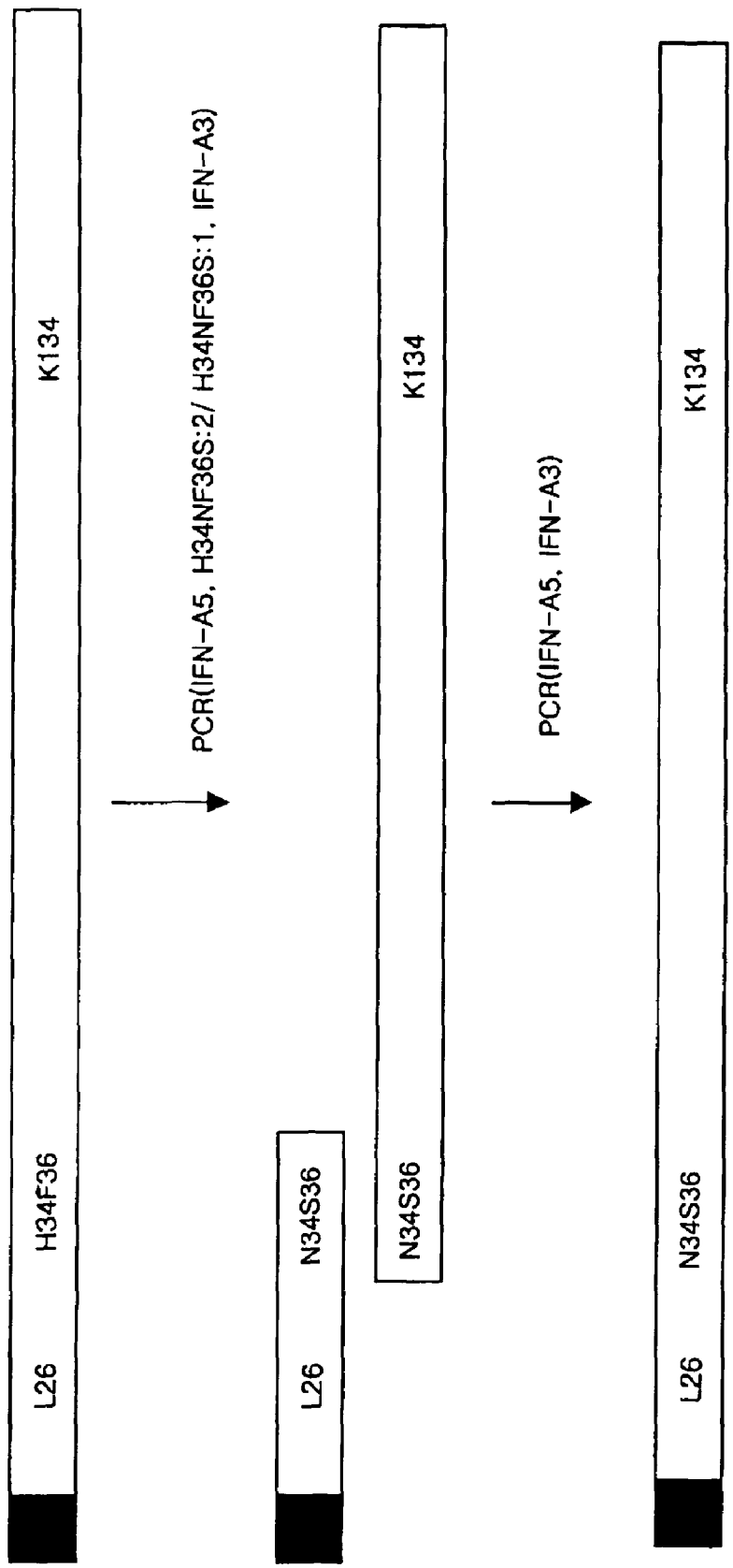
FIG. 4 is a schematic diagram showing the method for modifying His34 and Phe36 with asparagine and serine, respectively.

(2) Construction of H34NF36S Modified Human Interferon Alpha Derivative (FIG. 4)

Using the same method for the L26N modified human interferon alpha derivative, human interferon alpha gene was amplified by PCR with synthetic oligodeoxynucleotides IFN-A5 and H34NF36S:2, and H34NF36S:1 and IFN-A3 to prepare DNA fragments.

Each of the DNA fragments was purified and subjected to the same method as described above to prepare IFN-alpha H34NF36S modified gene, in which His34 was changed to asparagine and Phe36 was changed to serine.

Figure 5:
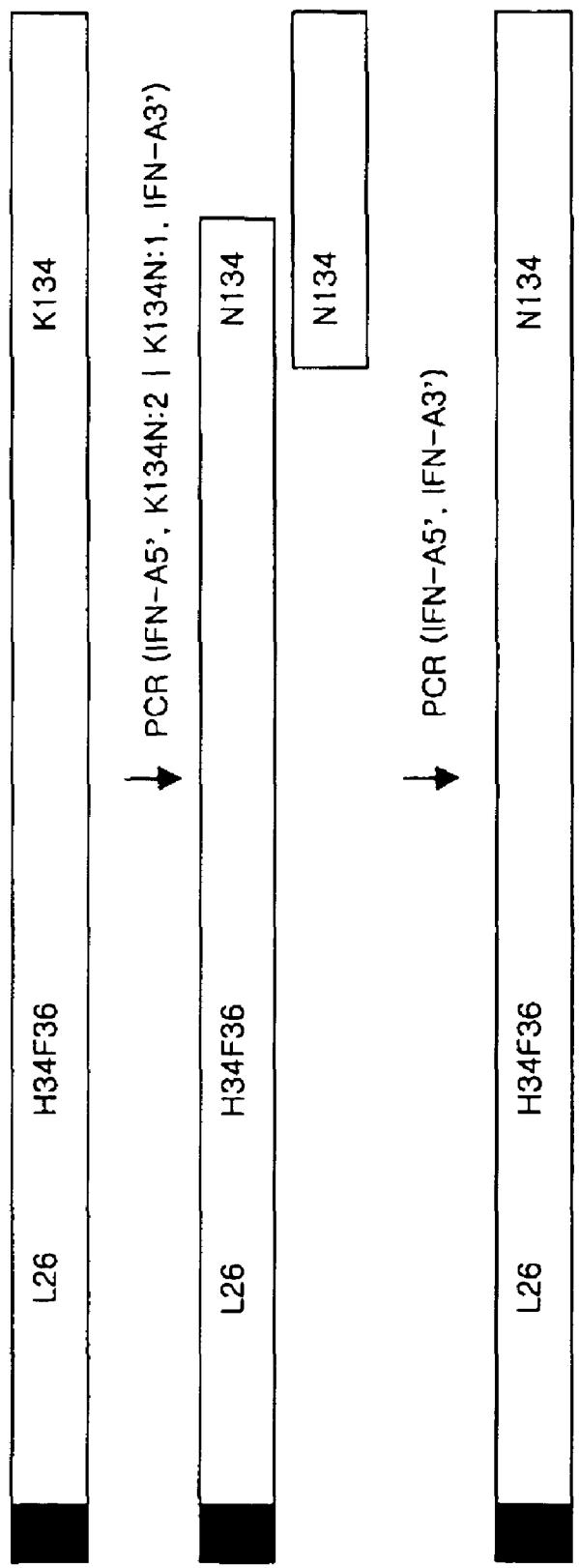
FIG. 5 is a schematic diagram showing the method for modifying Lys134 with asparagine.

(3) Construction of K134N Modified Human Interferon Alpha Isoform (FIG. 5)

Using the same method for the L26N modified modified human interferon alpha derivative, human interferon alpha gene was amplified by PCR with synthetic oligodeoxynucleotides IFN-A5' and K134N2, and K134N1 and IFN-A3' to prepare DNA fragments.

As a result, as shown in FIG. 4, two DNA segments substituted with a codon corresponding to asparagine instead of lysine at amino acid residue 134 were obtained.

The two DNA segments were subjected to secondary PCR using a primer pair of IFN-A5' and IFN-A3' to obtain a modified gene of IFN-alpha-K134N, in which amino acid residue 134 is modified with asparagine so that an additional glycosylation can take place.

Figure 6:
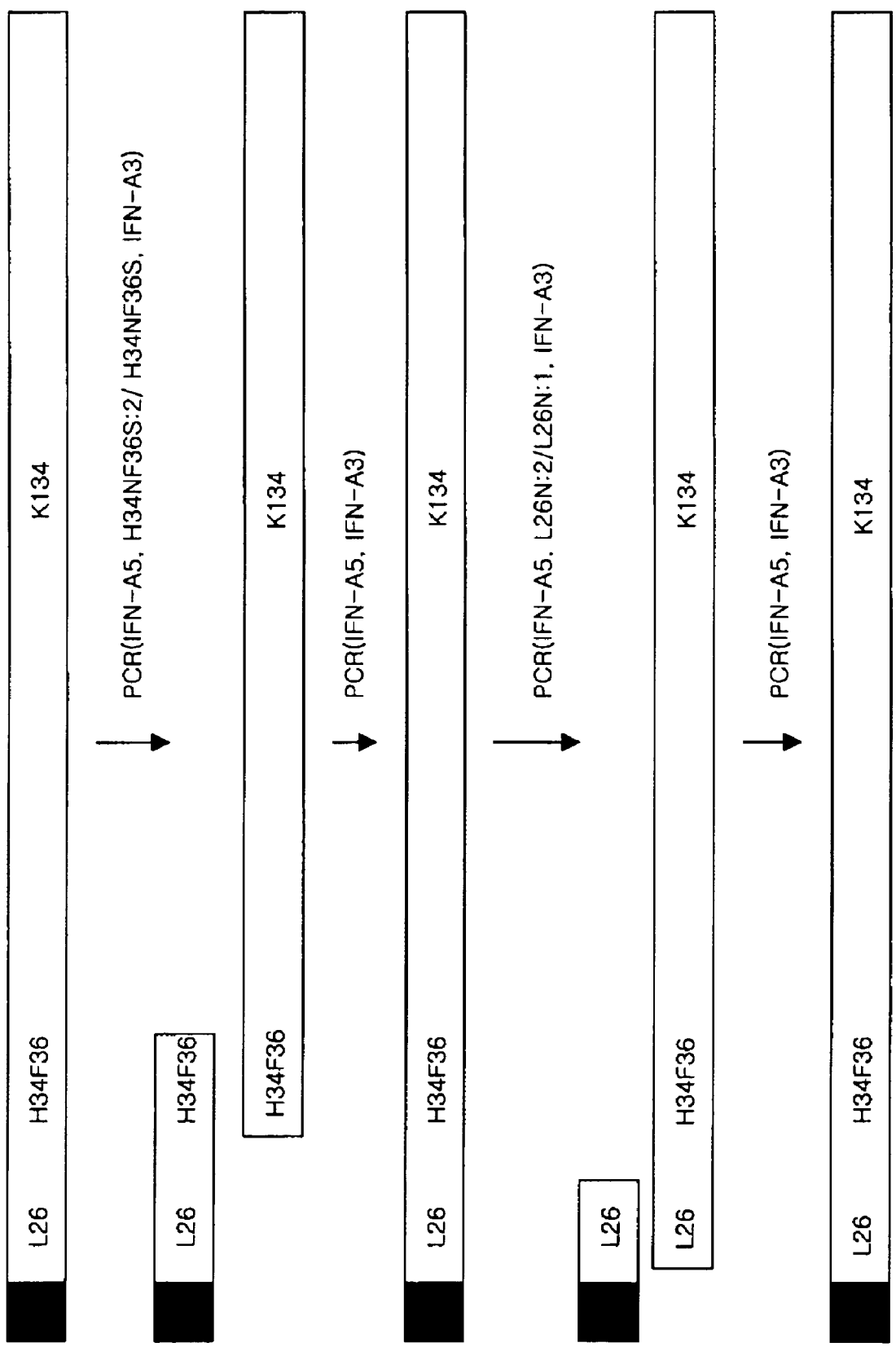
FIG. 6 is a schematic diagram showing the method for simultaneously modifying Leu26, Phe34, and Phe36 of wild-type interferon alpha with asparagine, asparagine and serine, respectively.

(4) Construction of Human Interferon Alpha Derivative with Both L26N and H34NF36S Modified (FIG. 6)

The same method for the L26N human interferon alpha derivative was followed using H34NF36S modified human interferon alpha derivative.

Figure 7:
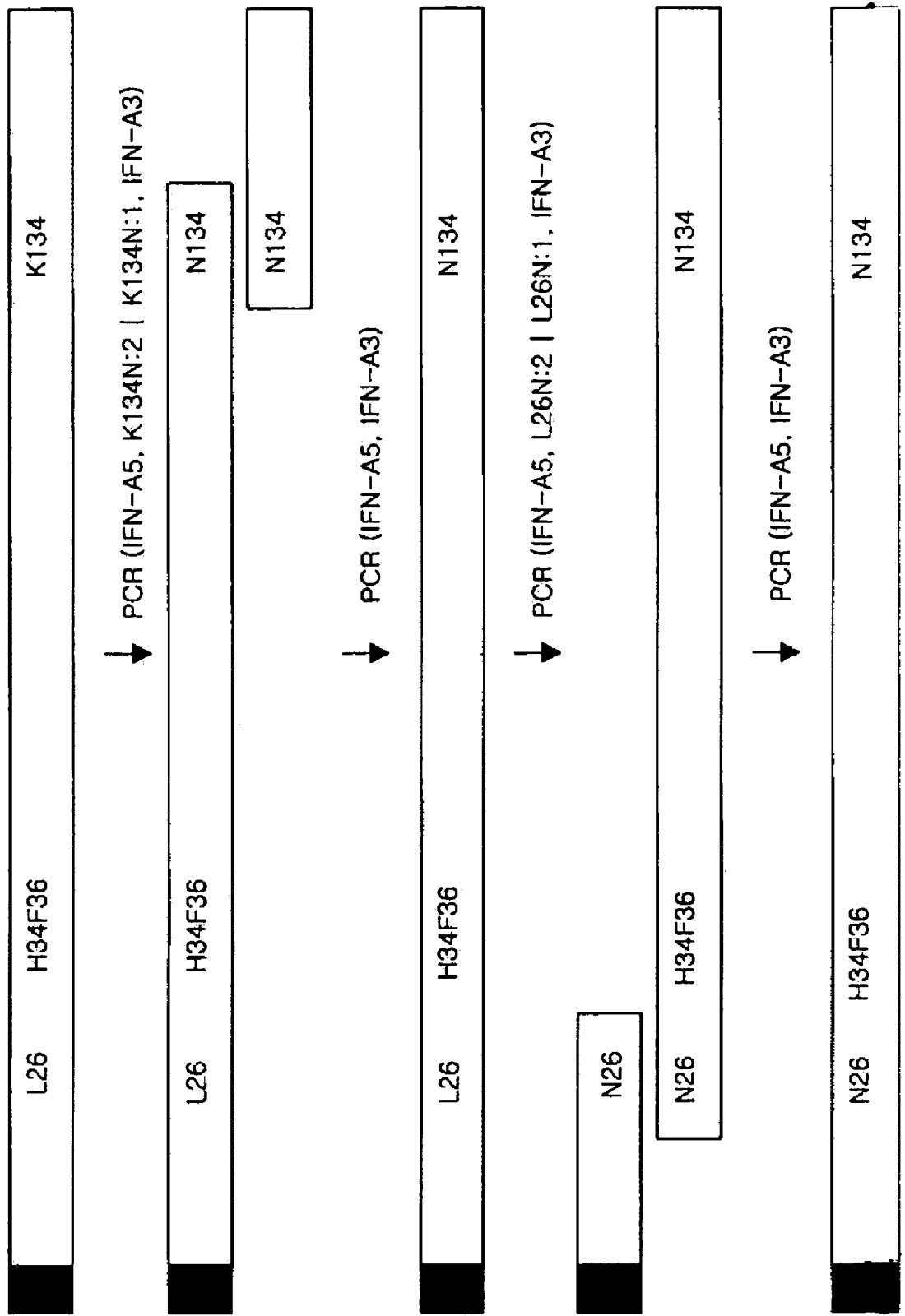
FIG. 7 is a schematic diagram showing the method for simultaneously modifying both Leu26 and Lys134 with asparagine.
Figure 8:
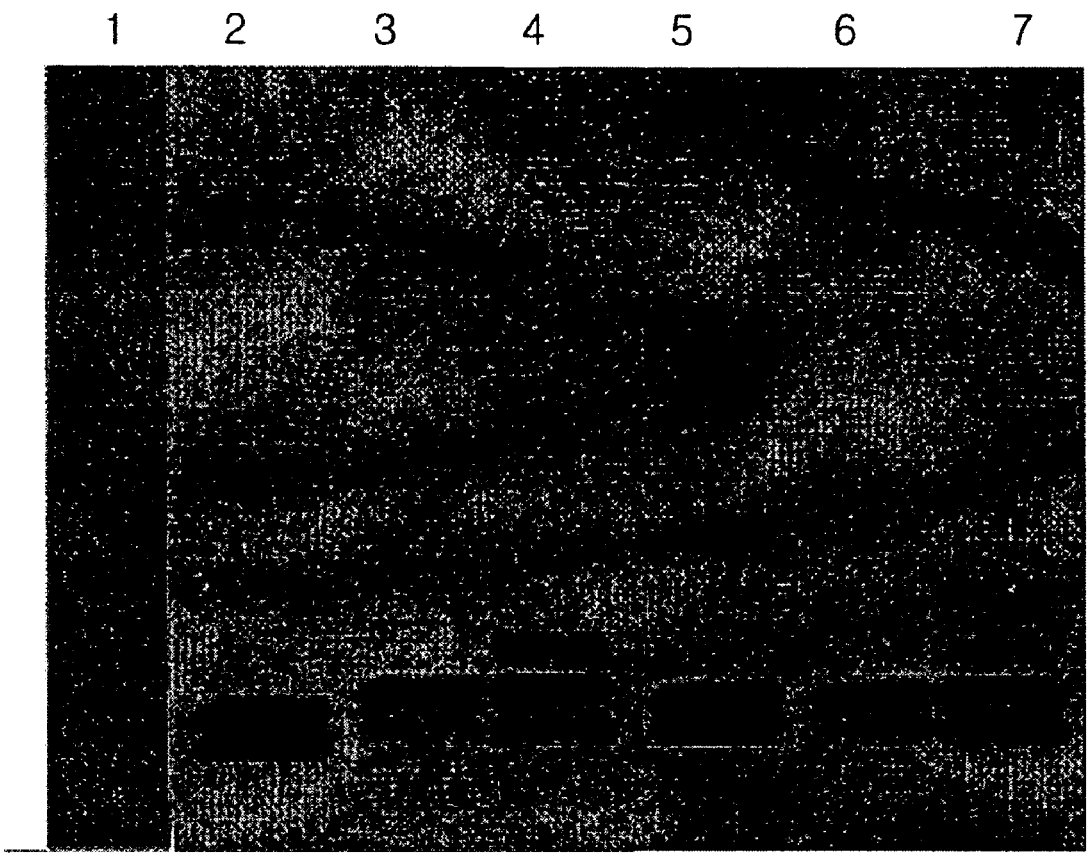
FIG. 8 shows the result of western blot on human interferon alpha derivatives. The primary antibody is a monoclonal antibody against for human interferon alpha and the secondary antibody is an antibody of rabbit antibody against mouse immunoglobuline bonded to HRP enzyme. Here, 1 represents a marker, 2 represents O-glycosylated IFN-alpha, 3 represents L26N mutant, 4 represents L26N/H34NF36S mutant, 5 represents H34NF36S mutant, 6 represents K134N mutant and 7 represents L26N/K134N mutant.
Figure 9:
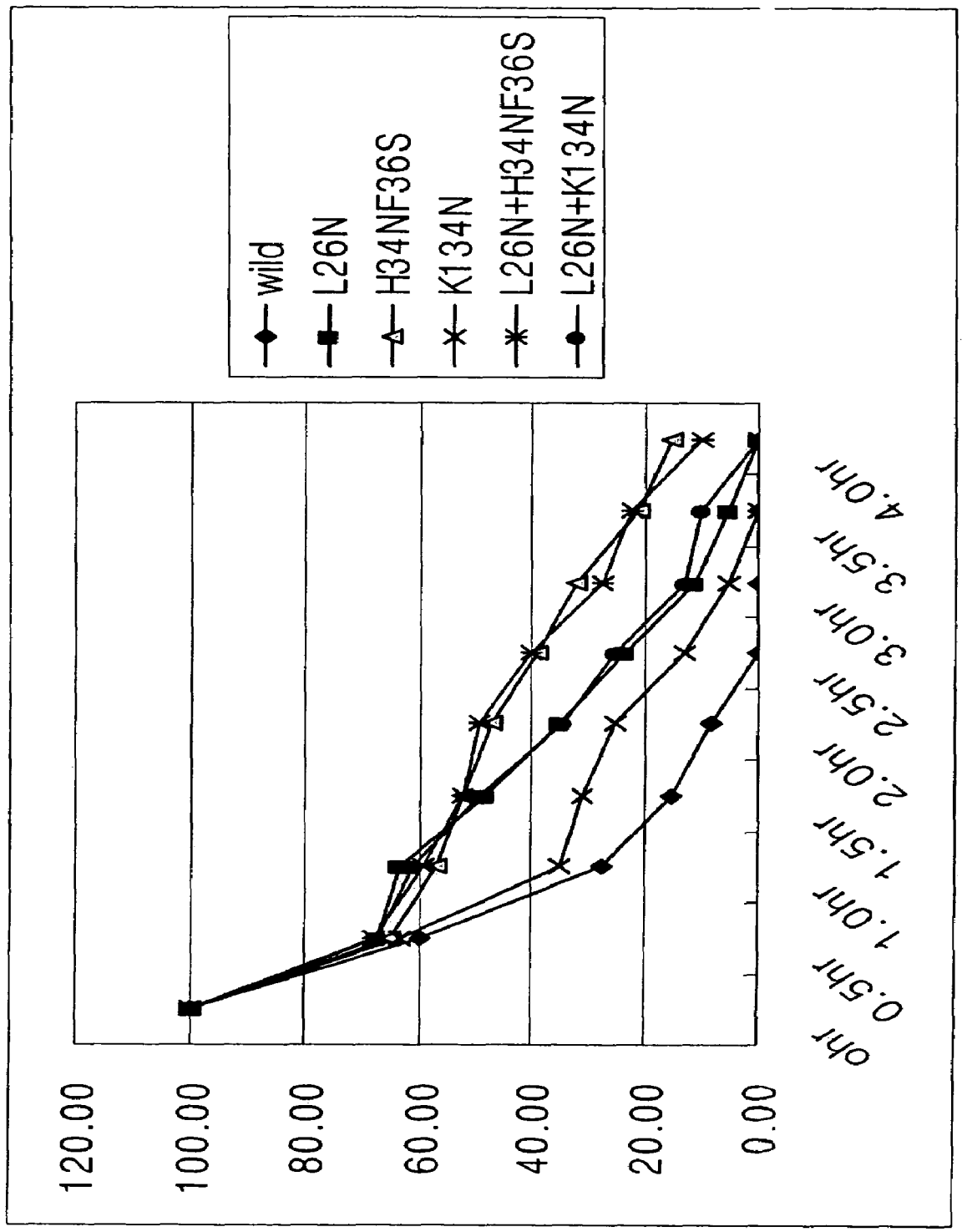
FIG. 9 is a graph showing the residual concentration of human interferon alpha derivatives in mouse according to elapsed time.

(5) Construction of Human Interferon Alpha Isoform with Both L26N and K134N Modified (FIG. 7)

The same method for the L26N modified human interferon alpha derivative was followed using K134N modified human interferon alpha isoform. In other words, 134th position was modified by the same method as shown in FIG. 5 and using the product as a template, 26th position was modified by the same method as shown in FIG. 3. As a result, a human interferon alpha gene with two sites modified at the same time was obtained.

Example 4

Transfection into CHO Cell and Expression

In a 60 mm cell culture dish, CHO cells (DG44) were raised to 40-80% confluent (1-4×10⁵cell/60 mm dish). 3 µl of Superfectin reagent (BM) and 97 µl of cell culture medium (α-MEM with media, serum-free, antibiotic-free) were thoroughly mixed and human interferon alpha derivative expression vector DNA (0.1 µug/µl or more, about 2 ug) and vector pLTRdhfr26 (ATCC37295, about 0.2 µg) containing dhfr were added thereto. After the reaction was left for 5 to 10 minutes at room temperature and added to the prepared cells. After one day, the medium was exchanged with a medium containing 200 µg/ml of hygromycine (α-MEM without media, 10% FBS) and cultured for about 7 to 10 days. In the medium containing hygromycine at a concentration of 200 µug/ml, cell lines with human interferon alpha derivative introduced were selected. Each of the selected cell lines was cultured and confirmed for expression of human interferon alpha derivative by using a human interferon alpha (Hu-IFN-α) Multi-Specific ELISA Kit (PBL, Product No. 41105-1;).

Example 5

Purification of Human Interferon Alpha Derivative

The human interferon alpha derivatives expressed in CHO cells were purified by condensing the culture fluid using Centriprep (Mw Cut 10,000, Milipore) and subjecting to metal affinity purification using ProBond Purification System (Invitrogen).

Example 6

Pharmacokinetic Test in Rat

In order to confirm whether the purified interferon alpha derivatives could be sustained in actual living hosts, Sprague Dawley rats were used. Animals were injected with human interferon derivatives in a dose of 1×10⁶ U/Kg body weight. Each group comprised 4 animals. In order to confirm blood concentration, blood was taken every 30 minutes. The blood samples were analyzed using an Human interferon Alpha (Hu-IFN-α) Multi-Specific ELISA Kit (PBL).

While the present invention has been described with reference to the particular illustrative embodiments, these embodiments may be modified without departing from the scope and spirit of the present invention.

We claim:

1. A recombinant human interferon alpha isoform comprising the amino acid sequence of SEQ ID NO: 1 that has been modified such that His at position 34 has been replaced by Asn and Phe at position 36 has been replaced by Ser.

2. A recombinant human interferon alpha isoform comprising the amino acid sequence of SEQ ID NO: 1 that has been modified such that His at position 34 has been replaced by Asn, Phe at position 36 has been replaced by Ser and Leu at position 26 has been replaced by Asn.

3. A recombinant human interferon alpha isoform comprising the amino acid sequence of SEQ ID NO: 1 that has been modified such that His at position 34 has been replaced by Asn, Phe at position 36 has been replaced by Ser and Lys at position 134 has been replaced by Asn.

4. A recombinant human interferon alpha isoform having the sequence of SEQ ID NO: 1 that has been modified such that His at position 34 has been replaced by Asn, Phe 36 at position has been replaced by Ser, Leu at position 26 has been replaced by Asn and Lys at position 134 has been replaced by Asn.

5. A pharmaceutical composition comprising the recombinant human intefferon alpha isoform according to any one of claims 1 to 4 and a pharmaceutically acceptable carrier.

* * * * *

SEQUENCE LISTING

<160> NUMBER OF SEQ ID NOS: 19

<210> SEQ ID NO 1
<211> LENGTH: 188
<212> TYPE: PRT
<213> ORGANISM: Artificial Sequence
<220> FEATURE:
<223> OTHER INFORMATION: Human interferon alpha isoform
<220> FEATURE:
<221> NAME/KEY: SIGNAL
<222> LOCATION: (1)...(23)
<223> OTHER INFORMATION: Propeptide

<400> SEQUENCE: 1

Met Ala Leu Thr Phe Ala Leu Leu Val Ala Leu Leu Val Leu Ser Cys
            -20                 -15                 -10

Lys Ser Ser Cys Ser Val Gly Cys Asp Leu Pro Gln Thr His Ser Leu
         -5                   1               5

Gly Ser Arg Arg Thr Leu Met Leu Leu Ala Gln Met Arg Arg Ile Ser
 10                  15                  20                  25

Leu Phe Ser Cys Leu Lys Asp Arg His Asp Phe Gly Phe Pro Gln Glu
                 30                  35                  40

Glu Phe Gly Asn Gln Phe Gln Lys Ala Glu Thr Ile Pro Val Leu His
                 45                  50                  55

Glu Met Ile Gln Gln Ile Phe Asn Leu Phe Ser Thr Lys Asp Ser Ser
             60                  65                  70

Ala Ala Trp Asp Glu Thr Leu Leu Asp Lys Phe Tyr Thr Glu Leu Tyr

```
            75                  80                  85
Gln Gln Leu Asn Asp Leu Glu Ala Cys Val Ile Gln Gly Val Gly Val
 90                  95                 100                 105

Thr Glu Thr Pro Leu Met Lys Glu Asp Ser Ile Leu Ala Val Arg Lys
                110                 115                 120

Tyr Phe Gln Arg Ile Thr Leu Tyr Leu Lys Glu Lys Lys Tyr Ser Pro
            125                 130                 135

Cys Ala Trp Glu Val Val Arg Ala Glu Ile Met Arg Ser Phe Ser Leu
        140                 145                 150

Ser Thr Asn Leu Gln Glu Ser Leu Arg Ser Lys Glu
    155                 160                 165

<210> SEQ ID NO 2
<211> LENGTH: 14
<212> TYPE: PRT
<213> ORGANISM: Artificial Sequence
<220> FEATURE:
<223> OTHER INFORMATION: Histidine tag

<400> SEQUENCE: 2

Gly Gly Ser His His His His His His Gly Asp Asp Asp Lys
  1               5                  10

<210> SEQ ID NO 3
<211> LENGTH: 585
<212> TYPE: DNA
<213> ORGANISM: Artificial Sequence
<220> FEATURE:
<223> OTHER INFORMATION: Human interferon alpha isoform

<400> SEQUENCE: 3
tcccaagctt atggccttga cctttgcttt actggtggcc ctcctggtgc tcagctgcaa      60
gtcaagctgc tctgtgggct gtgatctgcc tcaaacccac agcctggta gcaggaggac     120 cttgatgctc ctggcacaga tgaggcgcat ctctcttttc tcctgcttga aggacagaca    180
tgactttgga tttccccagg aggagttttgg caaccagttc caaaaggctg aaaccatccc    240
tgtcctccat gagatgatcc agcagatctt caatctcttc agcacaaagg actcatctgc    300
tgcttgggat gagaccctcc tagacaaatt ctacactgaa ctctaccagc agctgaatga    360
cctggaagcc tgtgtgatac aggggggtgg ggtgacagag actccctga tgaaggagga    420 ctccattctg ctgtgagga aatacttcca agaatcact ctctatctga aagaagaa      480 atacagccct tgtgcctggg aggttgtcag agcagaaatc atgagatctt tttctttgtc    540
aacaaacttg caagaaagtt taagaagtaa ggaatgagga tccca                     585

<210> SEQ ID NO 4
<211> LENGTH: 54
<212> TYPE: DNA
<213> ORGANISM: Artificial Sequence
<220> FEATURE:
<223> OTHER INFORMATION: Oligonucleotide primer

<400> SEQUENCE: 4
gtgctcagct gcaagtcaag ctgctctgtg ggctgtgatc tgcctcaaac ccac            54

<210> SEQ ID NO 5
<211> LENGTH: 54
<212> TYPE: DNA
<213> ORGANISM: Artificial Sequence
<220> FEATURE:
<223> OTHER INFORMATION: Oligonucleotide primer
```

<400> SEQUENCE: 5
atggccttga cctttgcttt actggtggcc ctcctggtgc tcagctgcaa gtca                54

<210> SEQ ID NO 6
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 6
tcccaagctt atggccttga cctttgcttt actg                34

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 7
tgggatcctc attccttact tcttaaactt tcttg                35

<210> SEQ ID NO 8
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 8
aagcttccca tgggggggttc tcatcatcat catcatcatg gg                42

<210> SEQ ID NO 9
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 9
catcatcatc atcatcatgg ggacgatgac gataag                36

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 10 acccccatg gagcccacag agcagcttga                30

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 11
ggggacgatg acgataagtg tgatctgcct caaacc                36

<210> SEQ ID NO 12

```
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 12
gcacagatga ggcgcatctc taacttctcc tgcttgaagg acaga          45

<210> SEQ ID NO 13
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 13
tctgtccttc aagcaggagt taagagagat gcgcctcatc tgtgc          45

<210> SEQ ID NO 14
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 14
ttgaaggaca gaaacgacag cggatttccc cag                       33

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 15
cttcatcagg ggagtctcgt tcaccccac ccc                        33

<210> SEQ ID NO 16
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 16
actctctatc tgaaagagaa gaactacagc ccttgtgcct gggag          45

<210> SEQ ID NO 17
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 17
ctcccaggca aagggctgt agttcttctc tttcagatag agagt           45

<210> SEQ ID NO 18
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 18
```

```
tcccaagctt atggccttga cctttgcttt actg                                    34

<210> SEQ ID NO 19
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 19
tgggatcctc attccttact tcttaaactt tcttg                                   35
```